United States Patent
Ashby, Jr.

(10) Patent No.: US 6,713,497 B1
(45) Date of Patent: Mar. 30, 2004

(54) USE OF VITAMIN B6 TO MITIGATE VISUAL FIELD DEFECTS ASSOCIATED WITH THE USE OF GABAERGIC DRUGS IN MAMMALS

(75) Inventor: Charles R. Ashby, Jr., Sound Beach, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 10/389,578

(22) Filed: Mar. 17, 2003

(51) Int. Cl.[7] .................... A61K 31/4415; A61K 3/197
(52) U.S. Cl. .................. 514/347; 514/350; 514/561
(58) Field of Search ............... 514/347, 35 D, 514/561

(56) References Cited

U.S. PATENT DOCUMENTS

| | | | |
|---|---|---|---|
| 4,002,758 A | 1/1977 | Bigou | 424/263 |
| 4,540,582 A | 9/1985 | Seiler et al. | 514/561 |
| 4,595,697 A | 6/1986 | Seiler et al. | 514/534 |
| 4,973,467 A | 11/1990 | Sahley | 424/439 |
| 4,980,168 A | 12/1990 | Sahley | 424/439 |
| 5,051,258 A | 9/1991 | Sahley | 424/439 |
| 5,189,064 A | 2/1993 | Blum et al. | 514/561 |
| 5,385,939 A | 1/1995 | Laties et al. | 514/554 |
| 5,567,731 A | 10/1996 | Laties et al. | 424/439 |
| 5,681,578 A | 10/1997 | Sahley | 424/439 |
| 6,057,368 A | 5/2000 | Dewey et al. | 514/561 |
| 2002/0048612 A1 | 4/2002 | Evans et al. | 424/752 |

OTHER PUBLICATIONS

Gardner et al., Synapse, 46(4), pp. 240–250 (Dec. 15, 2002) (abstract).*

Nabbout, R., Drug Safety, 24/11, pp. 813–28 (2001 (abstract).*

S. G. Mueller, O. M. Weber, P. Boesiger and H. G. Wieser, "Influence of pyridoxal 5′-phosphate alone and in combination with vigabatrin on brain GABA measured by 1H–NMR–spectroscopy", *Brain Research Bulletin*, vol. 55, No. 4, pp. 555–590 (2001).

* cited by examiner

*Primary Examiner*—Phyllis G. Spivack
(74) *Attorney, Agent, or Firm*—Margaret C. Bogosian

(57) ABSTRACT

The invention provides a method for treating visual field defects in a mammal in need thereof by administering an effective amount of vitamin B6 to the mammal.

8 Claims, No Drawings

USE OF VITAMIN B6 TO MITIGATE VISUAL FIELD DEFECTS ASSOCIATED WITH THE USE OF GABAERGIC DRUGS IN MAMMALS

This invention was made with Government support under contract number DE-AC02-98CH10886, awarded by the U.S. Department of Energy. The Government has certain rights in the invention.

BACKGROUND OF THE INVENTION

The invention relates to methods for treating mammals having excess gamma amino butyric acid (GABA) in the central nervous system (CNS). The invention is especially aimed at mammals having visual field defects as a result of excess GABA.

Certain drugs are known to increase GABA levels in the brain (i.e. GABAergic drugs). These drugs are well known to be effective in the treatment of conditions such as seizure disorders.

Recently, it has been discovered that some GABAergic drugs, for example, gamma vinyl GABA (GVG), are also effective for treating and preventing drug addiction. See U.S. Pat. Nos. 6,057,368 and 6,395,783 to Dewey et al., and pending U.S. patent application Ser. Nos. 09/189,166, 09/209,952, 09/362,592, and 09/853,548.

However, there are undesirable side effects, including visual disturbances, associated with the use of GABAergic drugs. In particular, there have been reports of visual field defects (VFDs) associated with the use of GVG. Although the mechanism responsible for GVG-induced VFDs is unknown, it is believed that GVG's visual toxicity may be related to a significant elevation of GABA levels within the retina. See Comaish, IF et al., "The effects of vigabatrin on electrophysiology and visual fields in epileptics: a controlled study with a discussion of possible mechanisms." Doc Opthalmol 104:195–212(2002);

It is known that GVG irreversibly inhibits the GABA-degrading enzyme GABA transaminase (GABA-T) and thereby induces an increase in brain GABA levels. It has also been shown that GVG-induced increases in GABA cause a decrease in glutamate decarboxylase (GAD), which is another GABA synthesizing enzyme.

To date, there have been no proposed strategies for treating or preventing the VFDs associated with the use of GABAegic drugs such as GVG. Therefore, there exists a need for a treatment for VFDs associated with the use of GABAergic drugs, such as GVG.

It is thus an object of the present invention to provide a composition and method for treating and/or preventing VFDs associated with the use of GABAergic drugs such as GVG.

SUMMARY OF THE INVENTION

The invention provides a method for treating visual field defects in a mammal in need thereof. The method includes administering an effective amount of vitamin B6 to the mammal.

According to the invention, the mammal is preferably a human. The vitamin B6 is administered in an amount from approximately 5 to 300 mg/day, preferably approximately 50 to 100 mg/day and more preferably approximately 10 to 50 mg/day.

In one embodiment of the invention, the mammal is being treated with gamma vinyl GABA for a drug addiction. In another embodiment, the mammal is being treated with gamma vinyl GABA for a seizure disorder.

In accordance with the invention, the vitamin B6 is administered before, simultaneously, or after administration of a GABAergic drug.

The invention also provides novel compositions which include a GABAergic drug and vitamin B6, preferably in a pharmaceutically acceptable carrier. In a preferred embodiment, the GABAergic drug is gamma vinyl GABA.

As a result of the present invention, a method is provided for treating visual field defects associated with excess GABA levels in the central nervous system of a mammal.

DETAILED DESCRIPTION OF THE INVENTION

The present invention is for a novel composition and a method for treating visual field defects in a mammal in need thereof. By "treating," is meant administering to a mammal a therapeutically effective amount of vitamin B6 so that the visual field defects are at least partially and/or substantially completely alleviated in the mammal. In addition, treating means administering a therapeutically effective amount of vitamin B6 so that the visual field defects are at least partially and/or substantially completely prevented from occurring in the mammal.

According to the invention, "a mammal in need thereof" is any mammal that has previously taken, is currently taking, or will be taking, a GABAergic drug.

A "GABAergic drug" is any compound that potentiates the GABAergic system or increases gamma amino butyric acid (GABA) levels in the central nervous system (CNS). According to the invention, the CNS includes the spinal cord, brain and midbrain regions. GABA is a widespread inhibitory neurotransmitter in the CNS. GABA is made in the brain from the amino acid glutamate with the aid of vitamin B6.

GABAergic drugs include compounds that enhance the production or release of GABA in the CNS and/or increase GABAergic transmission. In addition, a GABAergic drug is any compound that directly or indirectly augments or facilitates GABAergic neurotransmission in the CNS and/or the retina and/or the optic nerve.

These drugs include, but are not limited to, gabapentin, valproic acid, progabide, gamma-hydroxybutyric acid, fengabine, cetylGABA, topiramate, tiagabine, acamprosate (homo-calcium-acetyltaurine) or a pharmaceutically acceptable salt thereof, or an enantiomer or a racemic mixture thereof.

The present invention embraces compositions which include prodrugs of GABA or drugs which contain GABA as a moiety in its chemical structure. These prodrugs become pharmacologically active when metabolically, enzymatically or non-enzymatically biotransformed or cleaved into GABA in the CNS. An example of a prodrug of GABA is progabide which, upon crossing the blood brain barrier, increases endogenous CNS GABA levels.

A preferred GABAergic drug is gamma vinyl GABA (GVG). GVG is represented by the compound 4-amino-hex-5-enoic acid, and is sold under the product names Vigabatrin® and Sabril® by Hoechst-Marion Roussel. GVG is an irreversible inhibitor of the pyridoxal-phoshate dependent enzyme GABA transaminase (GABA-T) and is responsible for metabolizing GABA to succinic semialdehyde. GVG is also known to inhibit other transaminases, such as, for example, alanine aminotransferase and ornithine aminotransferase.

Not being bound by theory, it is believed that GVG's action results in an accumulation of GABA within the nerve terminal, and ultimately, an increase in synaptic GVG levels. GVG has also been reported to produce changes in the content/level of other amino acids in the brain such as, for example, a decrease in glutamate, aspartate and glutamine, and an increase in cerebrospinal fluid levels of homocarnosine.

GVG does not bind to any receptor or reuptake complex, but increases endogenous intracellular GABA levels by selectively and irreversibly inhibiting GABA-transaminase (GABA-T), the enzyme that normally catabolizes GABA.

As used herein GVG includes the racemic compound or mixture which contains equal amounts of S(+)-gamma-vinyl GABA, and R(−)-gamma vinyl GABA. This racemic compound of GVG is available as Vigabatrin® from Hoechst Marion Roussel and can be obtained from Marion Merell Dow of Cincinnati, Ohio.

GVG contains asymmetric carbon atoms and thus is capable of existing as enantiomers. The present invention embraces any enantiomeric form of GVG including the racemates or racemic mixture of GVG. In some cases there may be advantages, i.e. greater efficacy, to using a particular enantiomer when compared to the other enantiomer or the racemate or racemic mixture in the methods of the instant invention and such advantages can be readily determined by those skilled in the art.

For example, the enantiomer S(+)-gamma-vinyl GABA is more effective at increasing endogenous intracellular GABA levels than the enantiomer R(−)-gamma-vinyl GABA.

Different enantiomers may be synthesized from chiral starting materials, or the racemates may be resolved by conventional procedures which are well known in the art of chemistry such as chiral chromatography, fractional crystallization of diastereomeric salts, and the like.

According to the invention, a mammal in need thereof has, is, or will be taking a GABAergic drug for any condition that is treated by increasing gamma aminobutyric acid (GABA) levels and/or GABAergic transmission in the central nervous system regions. Such conditions include, for example, seizure disorders and drug addiction. Exemplary seizure disorders include, but are not limited to, epilepsy and West syndrome (i.e. infantile spasms).

"Drug addiction" is defined as addiction to one or more drugs of abuse. Drugs of abuse include, but are not limited to, stimulants such as cocaine, amphetamine, pipradol, methylphenidate, nicotine and caffeine, narcotics and pain medications such as morphine and methadone, and central nervous system depressants such as barbiturates, chlordiazepoxide and ethanol.

According to the present invention, addiction to a combination of one or more drugs of abuse is also a condition that is treated by administering a GABAergic drug.

A "mammal" suitable for the methods of the present invention is any mammal, including a human, domestic animal (e.g. cat or dog), laboratory animal (e.g. rat or monkey) or farm animal (e.g. cow, horse or pig). Most preferably the mammal is a human. All humans are contemplated, including infants, children and adults.

In accordance with the invention, "visual field defects" include any disturbance of the visual field. For example, visual field defects include loss of visual acuity, loss of peripheral vision, visual field constrictions, reduction in retinal cone function, bilateral concentric defect and optic neuropathy. Preferably, visual field defects are associated with the retina.

Vitamin B6 is a water-soluble vitamin that is suitable in any active form including, for example, pyridoxine, pyridoxal and pyridoxamine. Preferably, the vitamin B6 is a salt, such as pyridoxine HCL. The vitamin B6 is also suitable as pyridoxal phosphate.

The vitamin B6 is administered in any form including tablet, caplet, and liquid formulations. The vitamin B6 is administered systemically or optically (e.g. eye drops). Systemic administration can be achieved by any means known to the skilled practitioner, including enteral and parenteral administration. The vitamin B6 is also suitably administered nasally, transdermally or by nebulizer. Sustained release formulations are also contemplated by the invention, and are discussed below.

According to the invention, the vitamin B6 can be administered prior to, simultaneously with, or after administration of the GABAergic drug. For example, prior to beginning treatment with a GABAergic drug, a mammal can begin to take vitamin B6. The prior administration can begin any time from about one month to about one day before treatment with the GABAergic drug commences.

The mammal may or may not continue treatment with the vitamin B6 after treatment with the GABAergic drug ends. Such continued treatment can last for anytime up to one year after treatment with the GABAergic drug ceases.

In addition, the mammal can begin to take the vitamin B6 after treatment with the GABAergic drug has already commenced, and the mammal may or may not continue treatment with the vitamin B6 as discussed above.

Simultaneous administration is accomplished by beginning treatment of the GABAergic drug at the same time treatment with the vitamin B6 is commenced. With simultaneous administration, the mammal can cease taking the vitamin B6 at the same time the GABAergic drug is ceased, or the mammal can continue to take the vitamin B6 after cessation of the GABAergic drug, as described above.

According to the invention, "an effective amount" of vitamin B6 is administered to the mammal. An effective amount of vitamin B6 is an amount that is effective to treat and/or prevent visual defects associated with the use of a GABAergic drug.

As mentioned above, GABA transaminase (GABA-T) is the enzyme that normally catabolizes GABA. GABA-T requires vitamin B6 as a co-factor. Not being bound by theory, Applicant believes that an effective amount of vitamin B6 could be administered to a mammal in need thereof that would protect the mammal against the toxic effects of the GABAergic drug, without blocking the therapeutic effects of the drug.

For example, an effective amount of vitamin B6 for a human is from about 5 mg/day to about 300 mg/day. Preferably, the amount is from about 50 mg/day to about 100 mg/day. More preferably, the amount is from about 10 mg/day to about 50 mg/day.

In one embodiment of the invention, the mammal is being treated with gamma vinyl GABA (GVG) for a drug addiction. As mentioned above, GVG is a preferred GABAergic drug according to the invention. In this embodiment, the drug addiction involves one or more drugs of abuse. Drugs of abuse include any drug that has addictive liability including, but not limited, to those drugs discussed above.

In another embodiment, the mammal is being treated with GVG for a seizure disorder. In this embodiment, the seizure disorder can be any seizure disorder, including but not limited to those seizure disorders discussed above.

Novel compositions are also contemplated by the invention. These novel compositions consist essentially of a GABAergic drug and vitamin B6, in a pharmaceutically acceptable carrier. As discussed above, a suitable GABAergic drug is any such drug that increases GABA levels in the brain.

A preferred composition consists essentially of GVG and vitamin B6 in a suitable pharmaceutical carrier (vehicle) or excipient as understood by practitioners in the art.

Examples of pharmaceutically acceptable carriers and excipients include starch, milk, sugar, certain types of clay, gelatin, stearic acid or salts thereof, magnesium or calcium stearate, talc, vegetable fats or oils, gums and glycols.

The compositions of the invention may be administered by methods known in the art, typically, systemically. Systemic administration can be enteral or parenteral. Enteral administration is a preferred route of delivery of the compositions. Liquid or solid (e.g., tablets, gelatin capsules) formulations can be employed.

Administration can also be accomplished by a nebulizer or liquid mist. Optical administration is preferred (e.g. eye drops). Parenteral administration of the compositions of the invention (e.g., intravenous, intramuscular, subcutaneous injection) is also contemplated. Formulations using conventional diluents, carriers, etc. such as are known in the art can be employed to deliver the compound.

The compositions may be administered to the mammal by sustained release, as is known in the art. Sustained release administration is a method of drug delivery to achieve a certain level of the drug over a particular period of time.

Preferably, the composition contains a GABAergic agent in an amount which is effective for the purpose intended, such as treatment of seizure disorder or drug addiction, but has little or no adverse effects. For example, the amount of GVG in the composition is from about 15 mg/kg to about 2 g/kg or from about 15 mg/kg to about 600 mg/kg.

A composition containing gabapentin will include gabapentin in an amount from about 500 mg to about 2 g/day. Gabapentin is available as Neurontin® from Parke-Davis in the United States.

A composition containing valproic acid will include valproic acid in an amount from about 5 mg/kg to about 100 mg/kg/day. Valproic acid is available as Depakene® from Abbott in the United States.

A composition containing topiramate acid will include topiramate in an amount from about 50 mg to about 1 g/day. is available as Topamax® from McNeil in the United States.

A composition containing progabide will include progabide in an amount from about 250 mg to about 2 g/day. Progabide is available as Gabrene® from Synthelabo, France. The chemical formula of progabide is $C_{17}H_{16}N_2O_2$.

A composition containing fengabine will include fengabine in an amount from about 250 mg to about 4 g/day. Fengabine is available as SL 79229 from Synthelabo, France. The chemical formula of fengabine is $C_{17}H_{17}C_{12}NO$.

A composition containing gamma-hydroxybutyric acid will include gamma-hydroxybutyric acid in an amount from about 5 mg/kg to about 100 mg/kg/day. Gamma-hydroxybutyric acid is available from Sigma Chemical. The chemical formula of gamma-hydroxybutyric acid is $C_4H_7O_3Na$.

GABAergic drug is meant to include the pharmaceutically acceptable salts of the drug. As used herein, pharmaceutically acceptable salts include those salt-forming acids and bases which do not substantially increase the toxicity of the compound. Some examples of suitable salts include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g. p-toluenesulfonic acids, and the like.

The vitamin B6 in the composition can be in any of the forms discussed above. Preferably the vitamin B6 is pyridoxine HCL. The amount of vitamin B6 in the composition will vary with the amount of GABAergic drug and the mammal being treated. In general, a suitable amount of vitamin B6 for a human is from about 5 mg/day to about 300 mg/day. Preferably, the amount is from about 50 mg/day to about 100 mg/day. More preferably, the amount is from about 10 mg/day to about 50 mg/day.

What is claimed is:

1. A method for treating visual field defects in a mammal in need thereof comprising administering an effective amount of vitamin B6 to the mammal, wherein the amount of vitamin B6 is about 50 mg/day to about 100 mg/day.

2. The method according to claim 1, wherein the mammal is a human.

3. The method according to claim 1, wherein the mammal is being treated with gamma vinyl GABA for a drug addiction.

4. The method according to claim 1, wherein the mammal is being treated with gamma vinyl GABA for a seizure disorder.

5. The method according to claim 1, wherein the vitamin B6 is administered before, simultaneously or after administration of a GABAergic drug.

6. A method for treating visual field defects in a mammal in need thereof comprising administering an effective amount of vitamin B6 to the mammal, wherein the amount of vitamin B6 is about 10 mg/day to about 50 mg/day.

7. A method for treating visual field defects in a mammal that has, is, or will be taking a GABAergic drug without blocking therapeutic effects of the GABAergic drug, the method comprises administering vitamin B6 in an amount of about 50 mg/day to about 100 mg/day to the mammal.

8. A method for treating visual field defects in a mammal that has, is, or will be taking a GABAergic drug, without blocking therapeutic effects of the GABAergic drug, the method comprises administering vitamin B6 in an amount of about 10 mg/day to about 50 mg/day to the mammal.

* * * * *